US008708699B2

(12) United States Patent
Suter et al.

(10) Patent No.: US 8,708,699 B2
(45) Date of Patent: Apr. 29, 2014

(54) DRILL GUIDE

(75) Inventors: Edmund Suter, Niederdorf (CH);
Steffen Kuehne, Moehlin (CH); Patrick Streff, Weil am Rhein (DE)

(73) Assignee: Straumann Holding AG, Basel (CH)

( * ) Notice: Subject to any disclaimer, the term of this patent is extended or adjusted under 35 U.S.C. 154(b) by 268 days.

(21) Appl. No.: 12/636,944

(22) Filed: Dec. 14, 2009

(65) Prior Publication Data
US 2010/0151411 A1 Jun. 17, 2010

(30) Foreign Application Priority Data

Dec. 15, 2008 (EP) .................................... 08021712

(51) Int. Cl.
*A61C 3/00* (2006.01)
(52) U.S. Cl.
USPC .............................................. 433/75; 606/96
(58) Field of Classification Search
USPC .................................. 433/72, 74–76; 606/96
See application file for complete search history.

(56) References Cited

U.S. PATENT DOCUMENTS

| 5,015,183 | A | | 5/1991 | Fenick | |
|---|---|---|---|---|---|
| 5,133,660 | A | | 7/1992 | Fenick | |
| 5,302,122 | A | * | 4/1994 | Milne | 433/76 |
| 5,320,529 | A | | 6/1994 | Pompa | |
| 5,718,579 | A | * | 2/1998 | Kennedy | 433/75 |
| 5,741,133 | A | * | 4/1998 | Gordils et al. | 433/76 |
| 5,743,916 | A | * | 4/1998 | Greenberg et al. | 606/102 |
| 5,769,636 | A | * | 6/1998 | Di Sario | 433/213 |
| 5,769,856 | A | * | 6/1998 | Dong et al. | 606/96 |
| 5,800,168 | A | * | 9/1998 | Cascione et al. | 433/75 |
| 5,888,034 | A | | 3/1999 | Greenberg | |
| 5,888,065 | A | * | 3/1999 | Sussman | 433/76 |
| 5,915,962 | A | | 6/1999 | Rosenlicht | |
| 5,954,769 | A | | 9/1999 | Rosenlicht | |
| 6,022,356 | A | * | 2/2000 | Noyes et al. | 606/96 |
| 6,062,856 | A | * | 5/2000 | Sussman | 433/76 |
| 6,290,497 | B1 | * | 9/2001 | Di Emidio | 433/76 |
| 6,390,814 | B1 | * | 5/2002 | Gardiner | 433/75 |
| 6,869,283 | B2 | * | 3/2005 | Sussman | 433/76 |
| 7,473,259 | B2 | * | 1/2009 | Jacobs et al. | 606/148 |
| 7,594,918 | B2 | * | 9/2009 | Brock | 606/99 |

(Continued)

FOREIGN PATENT DOCUMENTS

| DE | 299 09 616 U1 | 6/1999 |
|---|---|---|
| DE | 2006 004 954 U1 | 7/2006 |

(Continued)

OTHER PUBLICATIONS

Jun. 2, 2009 Search Report and Office Action in corresponding EP No. 08021712.8-2318.

(Continued)

*Primary Examiner* — Hao D Mai
(74) *Attorney, Agent, or Firm* — Novak Druce Connolly Bove + Quigg LLP

(57) ABSTRACT

Drill guide (1) for use in the dental field, comprising a grip (10), a bearing surface intended to bear at least partially on a template (50) or a drill sleeve (55), and at least one guide sleeve (20) having a longitudinal slit (30). The grip (10) has a top face and an underside. The at least one guide sleeve (20) is essentially hollow and cylindrical, has an upper end and a lower end, and protrudes from the underside of the grip (10).

32 Claims, 3 Drawing Sheets

(56) References Cited

U.S. PATENT DOCUMENTS

| | | |
|---|---|---|
| 7,942,668 B2 * | 5/2011 | Brajnovic et al. ............... 433/76 |
| 2003/0157457 A1 | 8/2003 | Blacklock |
| 2004/0013999 A1 * | 1/2004 | Sussman ......................... 433/75 |
| 2004/0048225 A1 * | 3/2004 | Fletcher ........................... 433/76 |
| 2004/0142300 A1 | 7/2004 | Aravena |
| 2004/0219477 A1 | 11/2004 | Harter |
| 2004/0219479 A1 | 11/2004 | Malin et al. |
| 2004/0219481 A1 | 11/2004 | Malin et al. |
| 2005/0106531 A1 * | 5/2005 | Tang .............................. 433/76 |
| 2005/0170311 A1 | 8/2005 | Tardieu et al. |
| 2006/0240378 A1 | 10/2006 | Weinstein et al. |
| 2006/0263743 A1 | 11/2006 | Tedesco |
| 2007/0077532 A1 | 4/2007 | Harter |
| 2008/0064005 A1 | 3/2008 | Meitner |
| 2008/0166681 A1 | 7/2008 | Weinstein et al. |

FOREIGN PATENT DOCUMENTS

| | | |
|---|---|---|
| DE | 10 2005 023 028 A1 | 11/2006 |
| EP | 1 894 539 A1 | 3/2008 |
| EP | 2 060 240 A2 | 8/2009 |
| JP | 2006-519038 | 9/2004 |
| JP | 2008-508931 | 2/2006 |
| JP | 2008-541928 | 12/2006 |
| WO | WO 94/00073 A | 1/1994 |
| WO | WO 97/43981 A1 | 11/1997 |
| WO | WO 97/49351 A1 | 12/1997 |
| WO | WO 03/071972 A1 | 9/2003 |
| WO | WO 2004-075771 A1 | 9/2004 |
| WO | WO 2005/053566 A1 | 6/2005 |
| WO | WO 2005/053567 | 6/2005 |
| WO | WO 2006/014130 A1 | 2/2006 |
| WO | WO 2008/089885 A | 7/2006 |
| WO | WO 2006/014130 | 9/2006 |
| WO | WO 2006/130067 A1 | 12/2006 |
| WO | WO 2007/067105 A1 | 6/2007 |
| WO | WO 2007/077223 A1 | 7/2007 |
| WO | WO 2007/079775 A1 | 7/2007 |
| WO | WO2007/104842 A1 | 9/2007 |
| WO | WO 2008/089885 | 7/2008 |

OTHER PUBLICATIONS

Documents listed herein were Oct. 16, 2013 Office Action in corresponding JP application (Not enclosed).
Jun. 27, 2013 First Office Action in corresponding China Application 200910260486.1 (English translation).

* cited by examiner

DRILL GUIDE

FIELD OF THE INVENTION

The present invention relates to a drill guide for use in the dental field.

BACKGROUND

To achieve a prosthetically optimized implant axis, a template, also called a drill-jig, is often used, e.g. an OP jig or CT splint. Templates are known for guiding dental implant drills for preparing the jaw bone and are intended to receive one or more dental implants. Templates of this kind are modeled manually or manufactured with the aid of a computer (CAM). They have drill holes that serve to guide a dental implant drill or the implant during a surgical intervention. Standardized metal drill sleeves (hereinafter standard drill sleeves) are often incorporated into the templates, e.g. polymerized in or pressed in, so as to increase the precision of the drilling operations. During a surgical intervention, the dental implant drill is guided by such a sleeve. The template thus serves to ensure that the drilling is carried out precisely in accordance with the optimal implant axes that have been determined at the planning stage.

In most implantation methods, the drilling is carried out in several steps. For example, a first drilling step is carried out with a pilot drill of small diameter, followed by a drilling step using a twist drill having the final diameter of the implant that is to be inserted. Depending on the method used, other drills, such as profile drills, with intermediate diameters or other cutting geometries may also be needed.

To apply this method, suitable reduction sleeves that correspond to the diameters of the dental drills used are fitted successively into the holes or standard drill sleeves of the templates. In the course of the drilling process, each one of the successive dental drills is inserted through the corresponding reduction sleeve and into the hole or drill sleeve.

The fact that the reduction sleeves are exchanged during the drilling process and that they typically have diameters of less than 6 mm, results in handling difficulties and even the risk of aspiration by the patient.

Reduction sleeves with grip-like extensions are known from WO 06/130067. The step-wise reduction in diameter is achieved by several reduction sleeves being stacked one inside another.

WO 06/014130 describes a reduction sleeve which is connected to a grip via a ball-and-socket hinge so as to be able to address different space situations in the patient's mouth.

WO 97/49351 discloses an implant-supported device for guiding a drill, with an auxiliary insert from which two reduction sleeves of identical diameter protrude and are held in a parallel position via a flat connection.

In order to achieve optimal guidance of the drill and thus optimal precision for the drilling process, the reduction sleeves need to have a certain height. This may lead to problems if the space above the implantation site is limited. Due to sterical hindrance, it may be difficult or even impossible to insert the dental drills through the reduction sleeves into the template.

In addition, the drilling portion of certain dental drills, in particular of profile drills, may be too wide for the reduction sleeve. In this case, it is not possible to insert the drill through the reduction sleeve and the drilling has to be performed without guidance. This may result in imprecise drilling and imperfect implant axes.

SUMMARY OF THE INVENTION

Various embodiments of the present invention make available an aid that is easy to handle, that can be used to reduce the diameter of the holes in templates, and/or, which can be used for sterically hindered implantation sites and for dental drills having wide drilling portions.

The drill guide according to one embodiment of the present invention is intended for use in the dental field. It comprises a grip, a bearing surface intended to bear at least partially on a template—also called a drill jig—or a drill sleeve, and at least one guide sleeve. The grip has a top face and an underside. The at least one guide sleeve is essentially hollow and cylindrical, has an upper end and a lower end, and is protruding from the underside of the grip. The at least one guide sleeve comprises a longitudinal slit, which extends from the upper end to the lower end of the guide sleeve. The slit is preferably parallel to the longitudinal axis of the guide sleeve. Typically, the width of the slit is constant over its entire length. However, it is also possible that the width of the slit is varied, the slit being wider at its top end and narrower towards its bottom end, for instance.

By means of the drill sleeve according to various embodiments of the present invention, it is possible to work with several drills having different diameters in one drill hole or drill sleeve, without the need for complicated handling of small reduction sleeves. The drill guide may also be suitable for dental drills having a drilling portion, which is wider than the guide sleeve's internal diameter. The shaft, or at least an "insertion area" of the shaft, of such a dental drill is usually narrower than the actual drilling portion. Hence, it is possible to insert the dental drill, for instance a profile drill, sideways into the drill guide by introducing the insertion area of the dental drill through the longitudinal slit of the guide sleeve. Thus, even dental drills having a particularly wide drilling portion can be guided by the drill guide of the present invention.

In addition, the drill sleeve may guarantee a prosthetically optimized implant axis even for sterically hindered implantation sites. Via the longitudinal slit in the guide sleeve, it is possible to insert the dental drill sideways into the guide sleeve. Thus, the space required above the implantation site can be minimized, which is particularly favorable if the space above the implantation area is limited and an axial insertion of the drill is difficult or even impossible.

Operating instruments used in surgery must be able to be reliably cleaned and sterilized. For this reason, one-part drill guides with smooth and accessible surfaces are preferred. Particular preference is given to one-part drill guides produced in one piece, since they do not have any connection points. However, multi-part drill guides with connection points that do not form gaps and that are easy to clean may also be suitable.

It is also advantageous to be able to use operating instruments that do not require adjustment or modification during the drilling process. The drill guides according to the present invention may also fulfill these conditions. In addition, they preferably have no undercuts and are easy to sterilize.

The drill guide according to one embodiment of the present invention may comprise one or several guide sleeves, preferably one or two. A drill guide with only one guide sleeve can be optimally adjusted to a patient's mouth with respect to length, angles and spatial requirement. On the other hand, a drill guide comprising two guide sleeves offers greater flexibility with respect to diameter and height. If the two guide sleeves have different internal diameters, for instance, a simple turning of the drill guide allows the surgeon to insert a guide sleeve of greater diameter into the template. With a matched set of two drill guides comprising two guide sleeves each, four different drill diameters are covered, which is sufficient for most dental drilling methods.

It is preferred that the guide sleeve is arranged at an end of the grip, and, in the case of a drill guide comprising two guide sleeves, the guide sleeves are preferably arranged at opposite ends of the grip. This allows the surgeon to employ the drill guide even in the back of the patient's mouth, where space is often very limited.

The at least one guide sleeve, which protrudes from the underside of the grip, may also protrude from the top side of the grip. It is possible to produce the at least one guide sleeve separately and to insert it into the grip, in which case the upper end of the guide sleeve is connected to the grip. However, it is preferable for the drill guide to be made in one piece, in order to ensure better sterilization.

The height of the at least guide sleeve determines, together with the geometry of the drilling tool, the precision of the drilling operation. Long guide sleeves increase the precision of the drill guide, but, at the same time, also increase the overall height of those parts of the template, drill guide, and drilling tool bearing on one another. Satisfactory results are achieved in select embodiments with guide sleeves having a height starting from 5 mm. Preferably, however, the height is not more than 20 mm.

The top end of the at least one guide sleeve serves as a drill stop for the drilling tool, i.e.

it ensures that the surgeon does not drill too deeply. This avoids damage to nerves during drilling. The drilling depth is determined by a distance d from the bearing surface of the drill guide to the top end of the at least one guide sleeve. The shorter the distance d, the deeper the drill can be inserted into the template and thus into the patient's bone. In addition, in case the drill guide is used in combination with a drill sleeve, the drilling depth is also determined by the distance from the top end of the drill sleeve to the bone surface. The closer the drill sleeve is arranged to the bone surface, the deeper is the drilling depth achieved. Therefore, the use of two or more drill guides with different distances d allows for:

a) the preparation of drill holes having different drilling depths, if the drill sleeves are arranged at the same distance from the bone surface; or b) the preparation of drill holes having the same drilling depths, if the drill sleeves are arranged at different distances from the bone surface and the distances d of the drill guides are chosen accordingly.

Preferably, the drill guide features a distance d of 1 mm to 10 mm, more preferably of 2.5 mm, 4.5 mm, or 6.5 mm.

For drill guides comprising two guide sleeves, it is preferred that the two guide sleeves have different distances d from the bearing surface to the top end of the guide sleeve. Preferably, both distances d are selected from the group consisting of 2.5 mm, 4.5 mm, and 6.5 mm.

The longitudinal slit in the guide sleeve is preferably narrower than one third, more preferably narrower than one quarter, of the guide sleeve's circumference. At the same time, the longitudinal slit has to be wider than at least part of the shaft of the dental drill and is preferably wider than the drilling portion of the dental drill. In a preferred embodiment, the longitudinal slit has a width of 1.2 mm to 2.2 mm, more preferably a width of 1.6 mm to 1.8 mm, for instance about 1.7 mm.

In a preferred embodiment, the longitudinal slit of the at least one guide sleeve is arranged vicinal to the grip. This allows for optimal positioning of the drill guide and lateral insertion of the dental drill into the guide sleeve from the outside of the patient's jaw. If a molar tooth has to be replaced, one may use a drill guide in which the longitudinal slit is arranged vicinal to the grip in the clockwise or counterclockwise direction, depending on the side of the face. Therefore, in the case of a drill guide comprising two guide sleeves, it is particularly preferred that the longitudinal slit of one guide sleeve is arranged vicinal to the grip in the clockwise direction, and the longitudinal slit of the other guide sleeve is arranged vicinal to the grip in the counterclockwise direction.

The at least one guide sleeve is essentially hollow and cylindrical and preferably has such an external diameter that it fits exactly into the drill holes of the template or into the corresponding standard drill sleeves.

In one embodiment, the internal diameter of the guide sleeve is adapted to the diameter of the dental drill. Thus, for each dental drill diameter, a different drill guide is chosen, the internal diameter of the guide sleeve corresponding to the drill's diameter. In a preferred embodiment, the internal diameter of the at least one guide sleeve corresponds to the standard diameters for drills for dental implants with diameters between 2 and 5 mm. Particularly preferred are internal diameters of 2.2, 2.8, 3.5, and 4.2 mm.

For drill guides comprising two guide sleeves, it is preferred that the two guide sleeves have different two internal diameters. For instance, one guide sleeve may have an internal diameter of 3.5 mm and the other guide sleeve may have an internal diameter of 4.2 mm.

Alternatively, all dental drills may include a guiding area, the diameter of which is identical and independent of the drilling diameter of the drill. During the drilling, the dental drill is guided by the drill guide, whereby the guiding area of the drill is interacting with the guide sleeve of the drill guide. In this case, it is not necessary to adapt the internal diameter of the guide sleeve to the drill's diameter, rather a single drill guide can be used for all drills used in the course of the drilling process.

The grip of the drill guide may be one-part or multi-part. It can be rigid or shapeable. It can also have a flat, semicircular or round profile. In order to ensure better sterilization, the surface is preferably smooth. The length of the drill guide is chosen such that the potential drilling sites in the jaw bone can be reached and the grip can preferably be grasped outside the oral cavity. A preferred grip of the drill guide has a length of between 5 and 12 cm.

Instruments used in dental implantology should take into account the dimensions and physiology of the patient's mouth. It may therefore be advantageous that the grip of the drill guide is angled and, in particular, that the grip has an S-shaped portion. In this way, the patient's tongue is given sufficient space under the instrument and is kept away from the drilling site by the grip lying above it. In addition, the drill guide is preferably also shaped such that it can be used anywhere in a partially toothed jaw. Therefore, the S-shaped portion of the grip is preferably arranged near the at least one guide sleeve, as close as possible to the guide sleeve. According to a further embodiment, the grip can be bent by hand, thus allowing for exact adjustment of the drill guide to the patient's physiology.

In drill guides comprising two guide sleeves, the guide sleeves are preferably parallel to one another on the grip. In this way, the overall height of the drill guide remains smaller. In other embodiments, the grip may be angled, this angled configuration preferably being arranged in the middle part of the grip. Such an angled configuration means that the guide sleeves are also at an angle to one another.

The drill guide according to one embodiment has a bearing surface, an essentially flat area, which is intended to bear on the template or the drill sleeve during the drilling process in order to provide greater stability and to prevent displacement of the drill guide during the drilling. If the bearing surface rests on the template, it preferably bears on the template directly adjacent to the implantation site.

In one embodiment of the present invention, the drill guide's bearing surface is formed by a part of the underside of the grip directly adjacent to the guide sleeve. Thus, when drilling the hole, the underside of the grip of the drill guide rests at least partially on the template or the drill sleeve. In this way, the dentist is provided with still greater stability during drilling, such that the drill does not slip.

In an alternative embodiment, the drill guide's bearing surface is formed by an essentially circular, radial protrusion on the guide sleeve. This radial protrusion is arranged at a predetermined distance 1 from the lower end of the guide sleeve and comprises a longitudinal slit corresponding to the longitudinal slit of the guide sleeve. Thus, the dentist is also provided with greater stability during drilling, whereby it is still possible to insert the drill sideways into the guide sleeve. Preferably, the radial protrusion extends to the upper end of the guide sleeve.

The preferred materials from which the drill guides of the present invention are made include stainless steel, titanium, and other metals customarily used in surgery. To increase the useful life of the drill guide, parts of the drill guide, for example the guide sleeve, can additionally be treated by surface-hardening techniques. One expedient technique for hardening stainless steel is Kolsterizing.

When using a plurality of drill guides, a coding arrangement can be employed. The color codes often used on the dental drills can be adopted for the drill guides and can be applied at a suitable location, for example on the grip near the corresponding guide sleeve. Alternatively, the guide sleeve itself can be painted in the appropriate color.

In another embodiment, a kit is provided comprising a template with drill holes and a drill guide according to one or more of the previously described embodiments. The template optionally contains one or more standard drill sleeves, which are inserted into the drill holes. In this kit, the guide sleeves of the drill guides are preferably adjusted to the drill holes or drill sleeves with regard to their external diameter and height. Thus, the external diameter of the at least one guide sleeve at its lower end matches the diameter of the drill holes in the template or the diameter of the standard dental drill sleeves contained in the drill holes of the template, respectively.

In another embodiment, several drill guides which have different internal diameters, distances d or alignments of the longitudinal slit, are made available in one set. In this case, preferably all the guide sleeves have different internal diameters, different distances d from the bearing surface to the top end of the guide sleeve, and/or different alignments of the longitudinal slits.

BRIEF DESCRIPTION OF THE DRAWINGS

Embodiments of the invention will be described, by way of example only, with reference to the accompanying drawings, in which.

DETAILED DESCRIPTION

Figure 1:
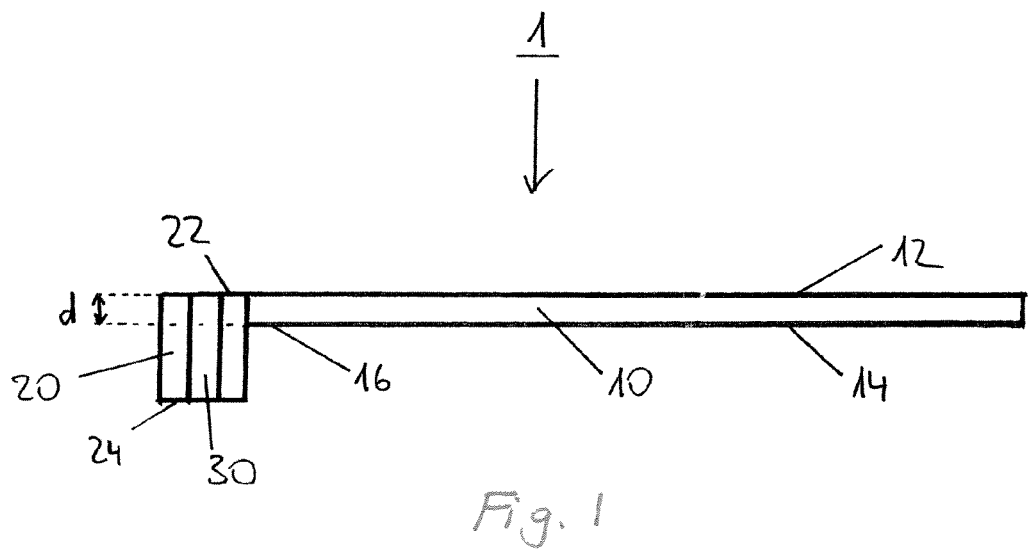
FIG. 1 shows schematically a side view of a first embodiment of a drill guide of the present invention.
Figure 2:
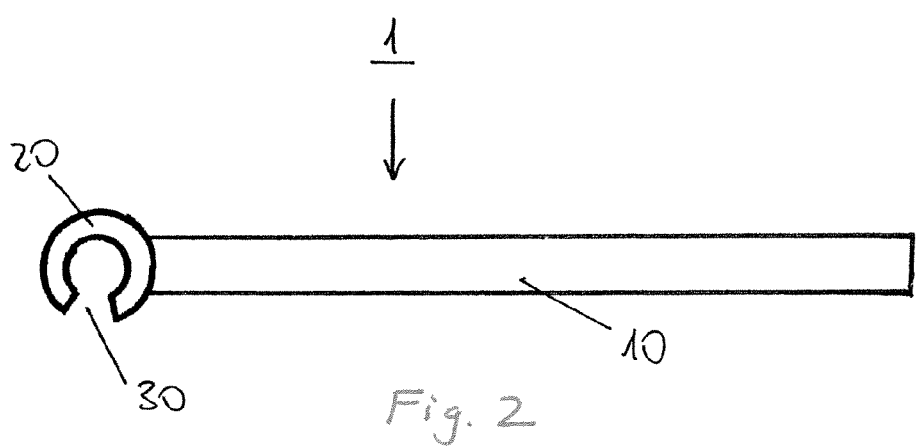
FIG. 2 shows schematically a top view of the drill guide of FIG. 1.

The drill guide 1 shown FIGS. 1 and 2 is made in one piece and consists entirely of stainless steel. It comprises a grip 10 and a guide sleeve 20, which is arranged at an end of the grip 10. The grip 10 has a top face 12 and an underside 14. The guide sleeve 20, which is protruding from the underside 14 of the grip 10, is essentially hollow and cylindrical and has an upper end 22 and a lower end 24. The guide sleeve 20 of the drill guide 1 has a longitudinal slit 30 extending from the upper end 22 to the lower end 24 of the guide sleeve 20. The longitudinal slit 30 is arranged vicinal to the grip 10, in the clockwise direction. The drill guide 1 further comprises a bearing surface 16, which is formed by a part of the underside 14 of the grip 10.

Figure 3:
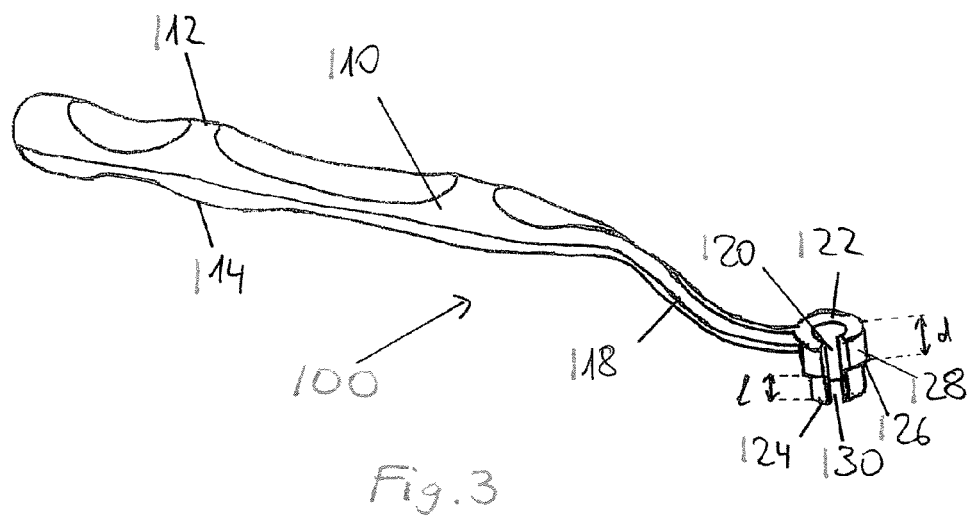
FIG. 3 shows schematically a perspective view of a second embodiment of a drill guide of the present invention.
Figure 4:
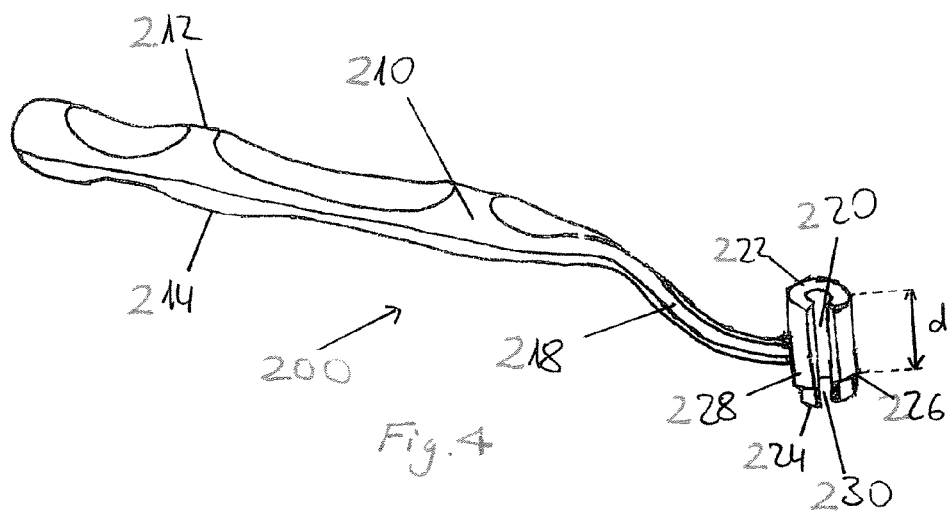
FIG. 4 shows schematically a perspective view of a third embodiment of a drill guide of the present invention.
Figure 5:
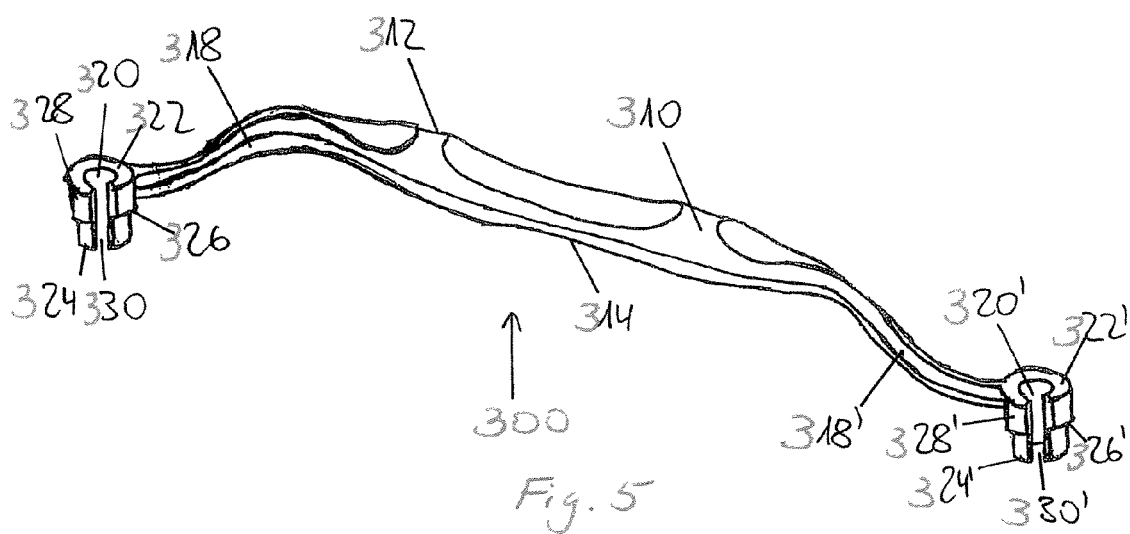
FIG. 5 shows schematically a perspective view of a fourth embodiment of a drill guide of the present invention.

FIGS. 3 to 5 show three further embodiments of the drill guide 100, 200, 300 (respectively) of the present invention with a grip 110, 210, 310 comprising one or two S-shaped portions 118, 218, 318, which are arranged near the guide sleeve(s) 120, 220, 320, 320'. In addition, the grip 110, 210, 310 is ergonomically designed to facilitate its handling. The guide sleeves 120, 220, 320, 320' of the drill guides shown in FIGS. 3 to 5 have an essentially circular, radial protrusion 128, 228, 328, 328', which is arranged at a distance 1 from the lower end 124, 224, 324, 324' of the guide sleeve and which also comprises a longitudinal slit corresponding to the longitudinal slit 130, 230, 330, 330' of the guide sleeve. The radial protrusion 128, 228, 328, 328' forms the bearing surface 126, 226, 326, 326' and extends to upper end 122, 222, 322, 322' of the guide sleeve. In contrast to the guide sleeve 120 of the drill guide 100 shown in FIG. 3, the guide sleeve 220 of the drill guide 200 shown in FIG. 4 also protrudes from the top side 212 of the grip 210. The drill guide 300 shown in FIG. 5, on the other hand, comprises two guide sleeves 320, 320', which are arranged at opposite ends of the grip 310. The longitudinal slit 330 of one guide sleeve 320 is arranged vicinal to the grip 310 in the clockwise direction, whereas the longitudinal slit 330' of the other guide sleeve 320' is arranged vicinal to the grip 320 in the counterclockwise direction.

Figure 6:
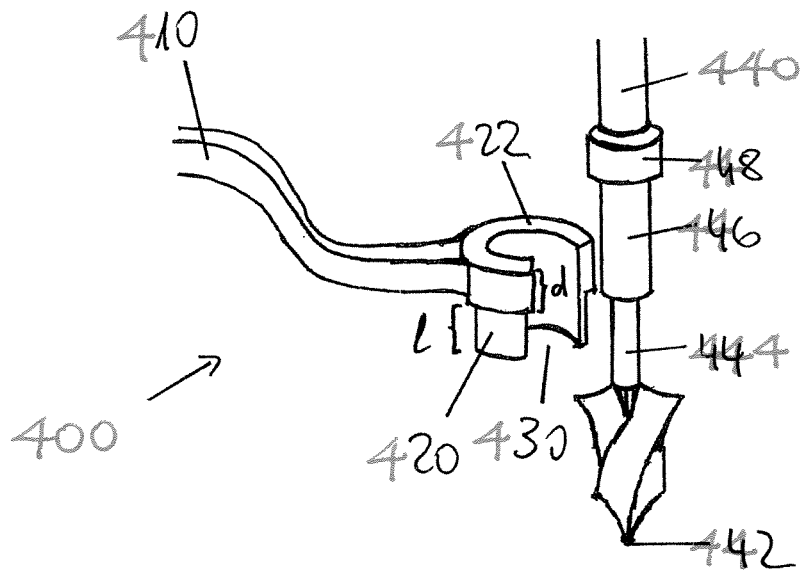
FIG. 6 shows schematically the insertion of a dental drill into an embodiment of a drill guide of the present invention.

FIG. 6 shows schematically the insertion of a dental drill 440 into the guide sleeve 420 of the drill guide 400. The depicted front end of the dental drill 440 has a drilling end 442, followed by an insertion area 445, a guiding area 446, and a drill stop 448. The insertion area 444 is narrower than the longitudinal slit 430 of the guide sleeve 420 in order to allow for lateral insertion of the drill 440 into the drill guide 400. The diameter of the guiding area 446 of the dental drill 440 corresponds to the internal diameter of the guide sleeve 420. During the drilling, the guiding area 446 of the dental drill 440 will be guided by the drill guide 400. The drill stop 448 is wider than the guiding area 446. During the drilling, the drill stop 448 will interact with the upper end 422 of the guide sleeve 420, thereby preventing the dental drill 440 from being inserted too far into the drill guide 400 and thus into the template.

Figure 7:
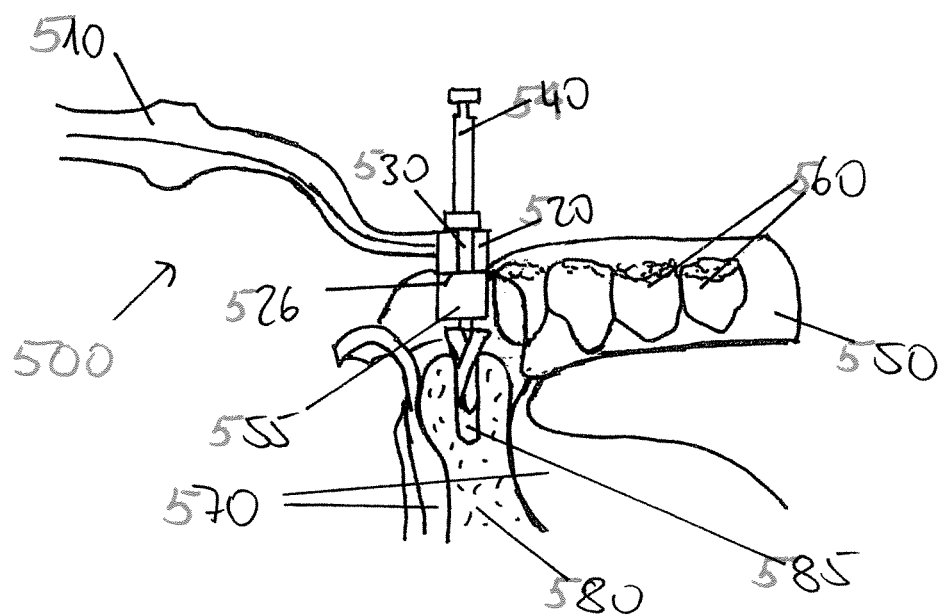
FIG. 7 shows schematically a perspective view of a drilling processing using an embodiment of a drill guide of the present invention.

FIG. 7 shows a schematic representation of a template 550, which is placed on a patient's dentition 560. The template 550 has a drill hole into which a standard drill sleeve 555 is inserted at the implantation position. Around the implantation site, the soft tissue 570 is folded back and the jaw bone 580 is laid open, in which a pilot hole 585 has been prepared. In order to further define the drill hole in the patient's jaw-bone 580 to the desired width, the drill guide 500 is held by its grip 510 and placed on the drill sleeve 555 with the bearing surface 526 resting on the drill sleeve's 555 upper end and the lower portion of the guide sleeve 520 is inserted into the drill sleeve 555. The dental drill 540 is then inserted through the guide sleeve 520 and the drill sleeve 555 into the pilot hole 585. During the drilling process, the dental drill 540 is then guided by the drill guide 500, the drill sleeve 555, and the template 550 in order to guarantee an optimal drilling axis.

The invention claimed is:

1. A drill guide and dental drill for use with the drill guide comprising:
   a dental drill having a drill shaft including a guiding area and a narrower insertion area,
   the drill guide comprising
      two guide sleeves;
      a grip, the grip having a top face and an underside and at least one of the guide sleeves protruding from the underside of the grip,
      each of the guide sleeves having a bearing surface formed by an essentially circular, radial protrusion on the guide sleeve intended to bear at least partially on a template or a drill sleeve, and the guide sleeve having a lower portion extending below the bearing surface having an external diameter that fits into a drill hole of a template or a drill sleeve,
      each of the guide sleeves being essentially hollow and cylindrical and having an upper end and a lower end, and each of the guide sleeves having an internal diameter sized to correspond to the guiding area of the drill shaft,
      wherein each of the guide sleeves have a longitudinal slit extending from the upper end to the lower end of the guide sleeve, and
      the longitudinal slit has a width greater than the insertion area of the drill shaft to allow for lateral insertion of the dental drill into the drill guide, and
      wherein a distance d from the bearing surface to the upper end of one of the two guide sleeves is different from a distance d' from the bearing surface to the upper end of the other of the two guide sleeves.

2. The drill guide and dental drill as claimed in claim 1, wherein the drill guide is made in one piece.

3. The drill guide and dental drill as claimed in claim 1, wherein at least one of the guide sleeves is arranged at an end of the grip.

4. The drill guide and dental drill as claimed in claim 1, wherein at least one of the guide sleeves also protrudes from the top face of the grip.

5. The drill guide and dental drill as claimed in claim 1, wherein the distance from the bearing surface to the upper end of at least one of the two guide sleeves is 2.5 mm, 4.5 mm, or 6.5 mm.

6. The drill guide and dental drill as claimed in claim 5, wherein both distances d, d' being selected from the group consisting of 2.5 mm, 4.5 mm, and 6.5 mm.

7. The drill guide and dental drill as claimed in claim 1, wherein the longitudinal slit of at least one of the guide sleeves has a width of 1.2 mm to 2.2 mm.

8. The drill guide and dental drill as claimed in claim 1, wherein the longitudinal slit of at least one of the guide sleeves has a width of 1.6 mm to 1.8 mm.

9. The drill guide and dental drill as claimed in claim 1, wherein the longitudinal slit of at least one of the guide sleeves is arranged vicinal to the grip.

10. The drill guide and dental drill as claimed in claim 1, wherein the longitudinal slit of one of the two guide sleeves is arranged vicinal to the grip in the clockwise direction, and the longitudinal slit of the other of the two guide sleeves is arranged vicinal to the grip in the counterclockwise direction.

11. The drill guide and dental drill as claimed in claim 1, wherein at least one of the guide sleeves has an internal diameter of 2.8 mm, of 3.5 mm or of 4.2 mm.

12. The drill guide and dental drill as claimed in claim 1, wherein the grip has an S-shaped portion near at least one of the guide sleeves.

13. The drill guide and dental drill as claimed in claim 1, wherein the grip can be bent by hand.

14. The drill guide and dental drill as claimed in claim 1, wherein the bearing surface is formed by a part of the underside of the grip directly adjacent to at least one of the guide sleeves.

15. The drill guide and dental drill as claimed in claim 1, wherein the radial protrusion is arranged at a predetermined distance 1 from the lower end of at least one of the guide sleeves and comprises a longitudinal slit corresponding to the longitudinal slit of the same guide sleeve.

16. The drill guide and dental drill as claimed in claim 15, wherein the radial protrusion extends to the upper end of the guide sleeve having the radial protrusion arranged at distance 1.

17. The drill guide and dental drill as claimed in claim 1, wherein the drill guide is made of stainless steel.

18. The drill guide and dental drill as claimed in claim 1, further comprising a template with drill holes, wherein an external diameter of at least one of the guide sleeves at its lower end matches a diameter of at least one of the drill holes in the template.

19. The drill guide and dental drill as claimed in claim 1, further comprising several drill guides, wherein all the guide sleeves have different distances from the bearing surface to the upper end of the guide sleeve.

20. The drill guide and dental drill as claimed in claim 18, further comprising at least one standard drill sleeve, wherein an external diameter of at least one of the guide sleeves at its lower end matches a diameter of the at least one standard drill sleeve.

21. The drill guide and dental drill as claimed in claim 1, wherein the at least one of the two guide sleeves has a drilling depth determined by a distance d from the bearing surface to the upper end of the guide sleeve.

22. The drill guide and dental drill as claimed in claim 21, wherein the drill guide is used in combination with the drill sleeve having distance d from the bearing surface to the upper end of the guide sleeve, and the drilling depth is also determined by a distance from an upper end of the drill sleeve to a bottom end of the drill sleeve having distance d from the bearing surface to the upper end of the guide sleeve.

23. The drill guide and dental drill as claimed in claim 1, wherein for at least one of the guide sleeves, the longitudinal slit is narrower than one third of the guide sleeve's inner circumference.

24. The drill guide and dental drill as claimed in claim 1, wherein for at least one of the guide sleeves, the longitudinal slit is narrower than one quarter of the guide sleeve's inner circumference.

25. The drill guide and dental drill as claimed in claim 1, wherein the two guide sleeves are positioned one at each end of the grip.

26. The drill guide and dental drill as claimed in claim 1, wherein the guide sleeves have different internal diameters.

27. The drill guide and dental drill as claimed in claim 1, wherein the guide sleeves have different drilling depths.

28. The drill guide and dental drill as claimed in claim 27, wherein the longitudinal slit of one of the guide sleeves is arranged vicinal to the grip in the clockwise direction, and the longitudinal slit of the other guide sleeve is arranged vicinal to the grip in the counterclockwise direction.

29. The drill guide and dental drill as claimed in claim 1, wherein the grip is angled.

30. The drill guide and dental drill as claimed in claim 1, wherein the grip has an s-shaped portion.

31. The drill guide and dental drill as claimed in claim 30, wherein the s-shaped portion is arranged near the at least one guide sleeve.

32. The drill guide and dental drill as claimed in claim 27, wherein the grip is angled between the guide sleeves.

* * * * *